United States Patent [19]
Manzo et al.

[11] Patent Number: 6,063,367
[45] Date of Patent: May 16, 2000

[54] PROTEIN EXTRACT FROM CEREAL GLUTEN, PREPARATION THEREOF AND USE THEREOF IN HAIR CARE

[75] Inventors: Robert Manzo, Goshen, N.Y.; Wilhelm Pickenhagen, Höxter; Jürgen Vollhardt, Bevern, both of Germany

[73] Assignee: Dragoco Gerberding & Co. A.G., Germany

[21] Appl. No.: 09/036,297

[22] Filed: Mar. 6, 1998

[30] Foreign Application Priority Data

Mar. 7, 1997 [DE] Germany .................. 197 09 360

[51] Int. Cl.[7] ...................................................... A61K 7/06
[52] U.S. Cl. ........................................ 424/70.1; 424/70.14
[58] Field of Search ............................... 424/70.1, 70.13, 424/70.14

[56] References Cited

U.S. PATENT DOCUMENTS 5,605,577  2/1997  Rayas et al. ............................ 127/67

*Primary Examiner*—Thurman K. Page
*Assistant Examiner*—Todd D Ware
*Attorney, Agent, or Firm*—Pendorf & Cutliff

[57] ABSTRACT

The invention describes a protein extract in the form of an alcoholic extraction solution obtained from dried cereal gluten, which solution has been treated with glycerol and/or a short-chain alkanediol and evaporated under reduced pressure until the alcohol content is less than 5% by weight, preferably less than 1% by weight.

This extract is outstandingly suitable for use in cosmetic preparations for care of damaged hair.

12 Claims, No Drawings

PROTEIN EXTRACT FROM CEREAL GLUTEN, PREPARATION THEREOF AND USE THEREOF IN HAIR CARE

BACKGROUND OF THE INVENTION

1. Field of the Invention

During the life cycle of a human hair, the hair structure is damaged to varying degrees as a result of mechanical stress, e.g. by combing or back-combing, or else as a result of chemical treatment, for example bleaching, colouring or perming. This damage impairs the surface properties of the hair, e.g. as regards gloss, suppleness or combability and generally reduces its strength. Damaged hair breaks more easily than undamaged hair.

2. Description of the Related Art

It has been known for some time that protein hydrolysates, which can be prepared by degradation of native proteins, have hair care properties. These hydrolysates chiefly contain peptides having a molecular weight in the range from 2–3 kDa and can be obtained from various protein sources, for example from cereal gluten by degreasing the gluten and then extracting it under alkaline conditions. As an example, the commonly assigned WO-A 90/05521 describes a hydrolysate which is obtained from cereal gluten, preferably wheat gluten, in a multi-stage process, and which can be used, inter alia, in hair care products. According to this specification, the dried gluten is firstly degreased using a fat solvent and then extracted using aqueous ethanol which has been rendered alkaline using $NH_3$. The extraction residue is discarded, and the liquid phase is cooled, if necessary under full vacuum, during which a protein product is precipated out which, after being separated off, forms a clear hydrolysate composition which, at room temperature, resembles honey. This composition can be conditioned and further processed for the desired purposes.

Hydrolysates of this type are absorbed by the hair relatively uniformly and are to be found not only in the outer cell layer of scales (cuticula) of the hair, but also in the region of the fibrous shaft (cortex). Such behaviour is very desirable for the more preventive care of still largely undamaged hair. For hair which is already more severely damaged, on the other hand, a care reagent is to be aimed at which is able to recognize the damaged site, to position itself there specifically and to counter the effects of the damage. The object of the invention is to provide such a care reagent.

SUMMARY OF THE INVENTION

This object is achieved according to the invention with a protein extract in the form of an alcoholic extraction solution obtained from dried cereal gluten, which solution has been treated with glycerol and/or a short-chain alkanediol and evaporated under reduced pressure until the alcohol content is less than 5% by weight, preferably less than 1% by weight.

A particularly advantageous protein extract is one which has been prepared by extracting the dried cereal gluten, preferably wheat gluten, using dilute short-chain alkanol, preferably ethanol, treating the liquid phase, following removal of the solid residue, with glycerol or, when required, a short-chain alkanediol, such as, for example, ethanediol or propanediol, and evaporating it under reduced pressure until the content of alkanol in the liquid phase has decreased to less than 5% by weight, preferably less than 1% by weight. Extraction is preferably carried out with 50–90%, preferably 60–70%, ethanol as extractant, the ratio of gluten to extractant being from 1:15 to 1:2, preferably 1:5, and at temperatures of 15–45° C., preferably at 20° C. The extraction time can be 0.25–48 h and is normally in the region of 15 h, depending on the equipment used. The protein content in the evaporated extract is 1–30% of protein, preferably 10% by weight of protein.

The invention and its preferred embodiments differ from WO-A 90/05521 both in terms of processing and also as regards the product. For example, a non-degreased gluten is subjected to extraction, which causes a higher content of lipids, glycolipids and phospholipids in the extract. Furthermore, the extraction is not carried out in the alkaline range, but in the neutral range, meaning that hardly any hydrolysis takes place and that protein fractions having a totally different composition are produced. Moreover, the proteins do not precipitate out from the extract either, making it impossible to prevent readily soluble components from becoming enriched in the supernatant of the precipitation and being discarded with the supernatant. Finally, the product according to WO-A 90/05521 is a honey-like composition, which is difficult to handle and, if appropriate, must be diluted with ethanol/water and then tends to form precipitates thus severely restricting further use. The product according to the invention, on the other hand, is a clear solution which has a very long shelf-life and which can be incorporated into cosmetic preparations without problems. Moreover, it contains no, or at least less than 5%, ethanol which, in higher concentrations, can in certain circumstances undesirably lower the flashpoint and the viscosity of cosmetic preparations.

It may be regarded as decisive that the protein extract according to the invention is not a protein hydrolysate, but essentially comprises the native cereal proteins (prolamines) (in the case of wheat therefore gliadin), which are virtually insoluble in water, compared with the hydrolysates, and whose main fraction has a molecular weight of 28–39 kDa. Surprisingly, it has now become evident that this product, differently from the hydrolysates, does not coat the hair with a uniform film and does not diffuse into deeper regions of the hair either, but binds primarily to damaged sites in human hair, particularly to split ends or to sections of hair damaged by combing or back-combing. The invention thus provides a care reagent suitable specifically for damaged hair.

DETAILED DESCRIPTION OF THE INVENTION

The following examples illustrate the invention.

EXAMPLE 1

Preparation of the Protein Extract

Commercially available, dried wheat gluten is extracted with 50–90%, preferably 60–70%, ethanol in a ratio of wheat gluten to solvent of from 1:15 to 1:2, preferably from 1:5, at 15–45° C., preferably at 20° C.

After the mixture has been stirred for 0.25–48 h, preferably 15 h, the suspension is freed from most of the solid phase using a decanter. The resulting decanted liquid is filtered until clear by filtration using a plate filter. The glycerol is then added and the mixture is evaporated under reduced pressure. Water and ethanol are distilled off until the bottom product contains less than about 1% ethanol. The resulting product can contain 1–30% by weight of protein and normally contains about 10% by weight of protein (dry substance).

In place of, or together with, ethanol, it is also possible to use methanol and/or isopropanol in appropriate dilution for the extraction, and the glycerol can be replaced in whole or in part by an alkanediol, such as ethanediol and/or propanediol.

EXAMPLE 2

Detection of Specific Adsorption on Human Hair 2.1 Preparation of the Fluorescently Labelled Protein The protein extracted from wheat gluten in Example 1 was rendered "visibles" by reacting it with fluorescein isothiocyanate (FITC 1 on Celite, Aldrich) at room temperature.

37.5 mg of FITC 1 were added to 1.5 g of protein, and the pH of the ethanol/water solution was adjusted to 8.5 using analytical grade triethylamine. The reaction mixture was stirred for 2 h at RT whilst being protected from light. The residue (Celite) was separated off by centrifugation (at 3,000 rpm, 10 min), and the supernatant was freed from low molecular weight FITC and any salts using a Sephadex LH-20 column. The fluorescing fractions were collected and evaporated on a rotary evaporator. Yield: 115 mg 2.2. Methods of Achieving Defined Hair Damage 2.2.1. Combing Tresses of hair 2 cm in width were each combed from root to tip for a total of 2,000 times (1,000 times from each side) using a compression moulded comb.

2.2.2. Back-Combing

A tress of hair 2 cm in width was back-combed from tip to root a total of 50 times using a compression moulded comb.

2.2.3. Bleaching 100 mg of human hairs, which were bound together to give a lock, were each treated in a solution of 9.6 ml of $H_2O$, 2.4 ml of $H_2O_2$ (30%), 0.57 mg of ammonium carbonate at pH 9.1 for 1 hour with gentle stirring at 30° C. in a thermostated bath. The hair was carefully washed with water and dried in air.

2.3. Treating the Hair with an Ethanolic Solution and Producing the Wash Liquor for the Investigation in 2.5.

The treatments were conducted on 10 hairs about 5 cm in length bound together to give a lock. The hair was treated with a solution of ethanol/water (70/30, v/v) containing 0.5% (m/v) of protein (fluorescently labelled as in 2.1) for 30 minutes with shaking at RT. The hair was rinsed using 25 ml.

2.4 Treatment with Aqueous Sodium Laureth Sulphate and Production of the Wash Liquor for the Investigation in 2.5.

The treatments were conducted on 10 hairs about 5 cm in length bound together to give a lock. The hair was treated with a solution of 5% (m/v) of SLS solution containing 0.5% (m/v) of protein (fluorescently labelled as in 2.1) for 30 minutes with shaking at RT. The hair was rinsed using 25 ml.

2.5. Fluorescence Spectroscopy

The wash liquors from 2.4. and 2.5. were subjected to fluorescence spectroscopy in an LS 50 luminescence spectrometer (Perkin-Elmer, Überlingen) in special quartz glass cuvettes (path length: 1 cm). All fluorescence measurements were made relative to a rhodamine 101 standard (3% in ethylene glycol). The excitation and emission slit was limited to 5.0 nm.

2.6. Result

TABLE 1

Fluorescence intensities $I_{max}$ (in %) of the wash liquor from 2.3. when using human hair pretreated as in 2.2. ($\lambda_{ex}$ = 494 nm)

| Hair | $I_{max}$ in % (at 522 nm) |
| --- | --- |
| untreated hair | 38.37 |
| bleached hair | 9.69 |
| hair combed 2,000 times | 9.16 |
| hair back-combed 50 times | 34.39 |

TABLE 2

Fluorescence intensities $I_{max}$ (in %) of the wash liquor from 2.4. when using human hair pretreated as in 2.2. ($\lambda_{ex}$ = 494 nm)

| Hair | $I_{max}$ in % (at 522 nm) |
| --- | --- |
| untreated hair | 112.87 |
| bleached hair | 12.33 |
| hair combed 2,000 times | 14.74 |
| hair back-combed 50 times | 16.20 |

The fluorescently labelled protein was held significantly more strongly to damaged hair and thus gave lower fluorescence intensities when it was washed out.

EXAMPLE 3

Fluorescence Microscopic Examination

Hair was treated with solutions of the fluorescently labelled protein as in Example 2.3. and Example 2.4. (without washing out) and then dried and subjected to the incident-light technique using fluorescence microscopy using an MPMO3 scanning photometer microscope (Zeiss, Oberkochen). The light source used was an extra-high-pressure mercury lamp. For the fluorescence microscopy, a special reflector which permitted fluorescence excitation at 450–490 nm and emission above a wavelength of 520 nm was used. The hair was embedded in immersion oil (Zeiss) for the fluorescence microscopic examination.

To prepare the fibre cross section, about 10 hairs were embedded in an acrylate resin (Historesin 0, Leica, Bensheim). After the resin had cured, fibre cross sections were prepared in sectional thicknesses of 20 $\mu$m using a Supercut 2050 rotary microtome(Leica).

From the microscope images, it is evident that the hair was not coated uniformly with protein. In particular, coating of the edges of the scales is observed. It is possible to detect a distinctly thicker coating on hair which has been predamaged mechanically, compared with untreated hair, particularly at the ends. Bleached hair shows a distinctly greater adsorption of the protein too.

Photographs of hair cross sections showed annular fluorescence phenomena, which indicate that the protein accumulates only in the outer region of the hair.

EXAMPLE 4

Example of the Effect of a Gliadin-Containing Protein Extract According to the Invention The investigations with the fluorescently labelled protein (gliadin) as in Examples 2 and 3 showed preferred deposition on damaged sections of hair. As a result, a strengthening of the hair is effected, which can be detected by a tensile stress test.

Hair and Pretreatment

European hair was used for this purpose, which is available in the form of locks 23 cm in length and about 2.4 g in weight. These locks were subjected, using standard methods simulating conditions met in practice, firstly to a bleaching operation, then in the smooth state to an alkaline permanent wave containing thioglycolic acid and, finally, to a washing operation with lauryl ether sulphate and a subsequent conditioning operation with 1% citric acid. The locks were then squeezed, dried under a drying hood with repeated combing and, finally, conditioned for 24 hours at 65% rel. humidity and 20° C.

Treatment with a Shampoo Based on a Protein Extract According to the Invention (gliadin shampoo)

For comparison purposes, the locks were then treated with a "gliadin shampoo" according to the invention and a non-inventive "placebo" shampoo. The locks were firstly wetted for 15 min and then "towel dried". The shampoos were applied in a ratio of 1 to 4, based on the weight of the dry locks and rubbed in for a total contact time of 3 min. The locks were then rinsed for 2–3 min in running water (about 35° C.) and dried as described above. This treatment was repeated 20 times.

Shampoo formulations

| Raw material (trade names) | INCI name | Gliadin shampoo Amount [%] | Placebo shampoo Amount [%] |
| --- | --- | --- | --- |
| Genapol LRO liquid | sodium laureth sulphate | 37.0 | 37.0 |
| Rewoteric AMB 14 | cocoamidopropyl betaine | 6.0 | 6.0 |
| Comperlan 100 | cocamide MEA | 0.5 | 0.5 |
| Citric acid | citric acid | 0.3 | 0.3 |
| Trilon B powder | tetrasodium EDTA | 0.1 | 0.1 |
| Sodium benzoate | sodium benzoate | 0.5 | 0.5 |
| Sodium chloride | sodium chloride | 1.8 | 1.8 |
| Perfume oil | fragrance | 0.5 | 0.5 |
| Gliadin solution according to the invention (9%) | — | 2.0 | 0.0 |
| Water | aqua | 51.3 | 53.5 |

Bundle Tensile Test

Measurements to determine the bundle tensile strength were carried out as in the standard IWTO-32-82 in water (wet) or under standard climatic conditions (dry=20° C., 65% rel. humidity). A total of 30 hairs were taken at random from locks for each product and combined to give a sample. 10 hairs were in each case removed from the sample and fixed parallel to one another in a special clamp. The individual ultimate tensile stress and elongation at break values were determined for a total of nine such sub-samples. After the test, in the case of the wet measurement, the samples were dried (50° C./12 h) and then reconditioned. The samples were weighed in order to determine the average cross sectional area of the hair in each sub-sample.

The tests were carried out as follows:

| | |
| --- | --- |
| * instrument: | INSTRON tensile testing machine |
| * clamped length: | 10 mm |
| * rate of elongation: | 10 mm/min |
| * full load: | 10N–20N |
| * medium: | in water (wet) or in standard climatic conditions (dry) |
| * number of hairs: | 9 × 10 |

Measurement Results

| | Average values ultimate tensile stress | | Average values ultimate tensile stress | |
| --- | --- | --- | --- | --- |
| | wet | dry | wet | dry |
| Gliadin shampoo | 60.5% | 54% | 155 MPa | 204 MPa |
| Placebo shampoo | 57.4% | 53.8% | 138 MPa | 189 MPa |

Interpretation

The inventive use of a protein extract, in the present example, the use of a protein extract based on gliadin ("gliadin solution") thus decisively increases the strength of the hair and counteracts damage, e.g. as a result of tearing during combing.

EXAMPLE 5

Hair Gloss Measurement

Test Method

Locks of hair were pretreated as in Example 4 and then treated with the inventive gliadin shampoo and the non-inventive placebo shampoo from Example 4 in accordance with the procedure contained therein.

A total of 10 hairs were taken at random from each of the locks for each shampoo product and measured in the central region at two points in each case. Measurement was carried out using a green-light laser (532 nm) at an incidence angle of 40° and simultaneous detection of the scattered light in an angle range of 50–170°. The hair is irradiated from root to tip.

Fitting two normal distributions to the scattered light profile makes it possible to determine the amount of specular (sR) and non-specular (nR) reflection. The gloss number Gl is calculated from:

$$Gl = sR/(nR+sR) \times 100\%$$

Measurement Results

| | Gloss number average values |
| --- | --- |
| Gliadin shampoo | 48.0% |
| Placebo shampoo | 40.1% |

Interpretation

The inventive use of a protein extract, in the example, the use of an extract based on gliadin, significantly increases hair gloss.

What is claimed is:

1. A process of preparing a protein extract, which comprises the steps of:
    (a) extracting dried cereal gluten under neutral conditions with an extraction medium comprising dilute alkanol so as to obtain a liquid extract comprising proteins, wherein the protein fraction of the extract consists essentially of prolamines;

(b) removing solid residue from the resulting liquid extract so as to produce a liquid phase;

(c) treating said liquid phase with a polyhydric alcohol selected from the group consisting of glycerol and a short chain alkanediol;

(d) concentrating the resultant treated liquid phase under reduced pressure until the resultant liquid concentrate has an alkanol content of less than 5% by weight.

2. Process according to claim 1, wherein said cereal gluten comprises wheat gluten.

3. Process according to claim 2, wherein said extraction medium is employed in a ratio of 15:1 to 2:1 relative to said gluten.

4. Process according to claim 3, wherein said ratio is about 5:1.

5. Processing according to claim 2, wherein said extraction medium contains 50 to 90% of ethanol.

6. Process according to claim 5, wherein said extraction medium contains 60 to 70% of ethanol.

7. Process according to claim 2, wherein said extraction is for at least 48 hours at a temperature of 15 to 45° C.

8. Process according to claim 7, wherein said temperature is about 20° C.

9. Process according to claim 1, wherein said alkanol content is less than 1% by weight.

10. A protein extract in the form of a concentration obtained by a process according to claim 1.

11. A method of treatment of damaged hair, which comprises (1) preparing a protein extract by a process comprising:
(a) extracting dried cereal gluten with an extraction medium comprising dilute alkanol so as to obtain a liquid extract;

(b) removing solid residue from the resulting liquid extract so as to produce a liquid phase;

(c) treating said liquid phase with a polyhydric alcohol selected from the group consisting of glycerol and a short chain alkanediol;

(d) concentrating the resultant treated liquid phase under reduced pressure until the resultant liquid concentrate has an alkanol content of less than 5% by weight, and (2) applying said concentrate to said damaged hair.

12. A process of preparing a protein extract, which comprises the steps of:

(a) extracting dried cereal gluten under neutral conditions with an extraction medium comprising dilute alkanol so as to obtain a liquid extract comprising proteins, wherein the protein fraction of the extract consists essentially of prolamines;

(b) removing solid residue from the resulting liquid extract so as to produce a liquid phase;

(c) treating said liquid phase with a polyhydric alcohol selected from the group consisting of glycerol and a short chain alkanediol;

(d) concentrating the resultant treated liquid phase under reduced pressure until the resultant liquid concentrate has an alkanol content of less than 5% by weight, wherein the amount of protein contained in the resultant liquid concentrate consists essentially of native cereal proteins.

* * * * *